Figure 1:
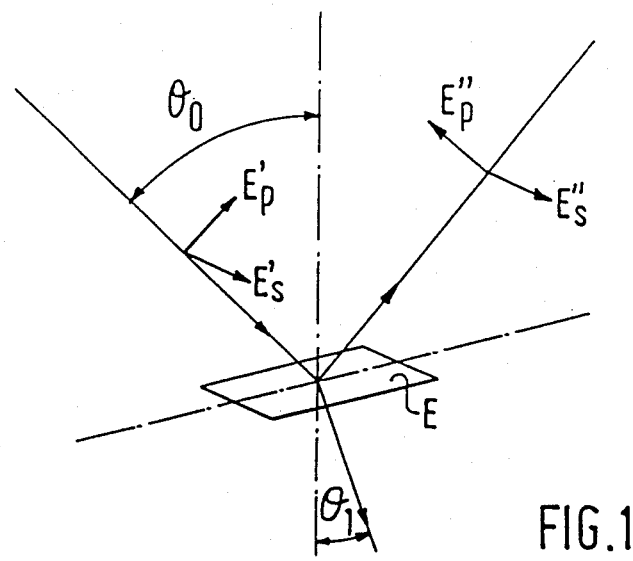

United States Patent [19]
Le Bris et al.

[11] Patent Number: 4,834,539
[45] Date of Patent: May 30, 1989

[54] SPECTROSCOPIC ELLIPSOMETER

[75] Inventors: Jean Le Bris, Quincy Sous Senart; Marko Erman, Paris, both of France

[73] Assignee: U.S. Philips Corporation, New York, N.Y.

[21] Appl. No.: 108,404

[22] Filed: Oct. 14, 1987

[30] Foreign Application Priority Data

Oct. 10, 1986 [FR] France .................. 86 14124

[51] Int. Cl.$^4$ .............................................. G01N 21/21
[52] U.S. Cl. ...................................... 356/369; 356/244
[58] Field of Search ............... 356/244, 327, 331, 332, 356/369; 350/531, 532

[56] References Cited

U.S. PATENT DOCUMENTS 4,210,401 7/1980 Batten .................................. 356/369

OTHER PUBLICATIONS

Gardner et al., "Automatic Infrared Ellipsometer for Characterizing Films on Multilayer Surfaces", *IBM Tech. Discl. Bull.*, vol. 16, No. 6, p. 1959, 11/73.

Primary Examiner—Davis L. Willis
Assistant Examiner—Matthew W. Koren
Attorney, Agent, or Firm—Paul R. Miller

[57] ABSTRACT

A spectroscopic ellipsometer comprises an illumination device having a focal point ($F'_2$) for illuminating a surface of a sample (E) in accordance with a given angle of incidence and a device for analyzing the light reflected from the surface of the sample. The sample support comprises three translation plates (20,30,40) in accordance with three respective directions ($T_2$, $T_3$, $T_1$). The translations in accordance with the first ($T_1$) and second ($T_2$) directions make it possible to realise cartographic representations of the sample (E) and the translation in accordance with the third direction ($T_3$) makes it possible to cause a point on the surface of the same (E) to coincide with the focal point ($F'_2$). Two plates ($PT_2$, 12) rotating about the axes $O_1$ and $O_2$, respectively, parallel to the first ($T_1$) and second ($T_2$) directions and intersecting each other at the focal point ($F'_2$) provide the possibility of orienting the sample (E) by means of rotation in two orthogonal planes about the focal point ($F'_2$).

7 Claims, 3 Drawing Sheets

SPECTROSCOPIC ELLIPSOMETER

The invention realtes to a spectroscopic ellipsometer comprising an illumination device having a focal point for illuminating a surface of a sample in accordance with a given angle of incidence, a device for analysing the light reflected from the surface of the sample, and a sample support by which a point on the surface of the sample can be made to coincide with the focal point.

In conventional ellipsometry plane waves are used with an angdular aperture of the luminious beam which does not exceed 1°. The Article "High Precision Scanning Ellipsometer" by D.E. ASPNES published in the magazine Applied Optics in January 1975 describes such an ellipsometer.

Ellipsometric techniques are also known in which convergent light is used for the purpose of obtaining both a good sensitivity to the condition of the surface of the sample and a high lateral resolution.

The article "Geometrical Resolution in the Comparison Ellipsometer" by STIBLERT et al. published in the Journal de Physique (Symposium C10, supplement to no 12, volume 44, December 1983) describes a comparison ellipsometer having a good sensitivity to the surface condition of the sample and a high lateral resolution of the order of 2 microns corresponding to the dimension of the spot illuminating the sample with convergent light. If the sensitivity to the surface condition is given by the presence of plane waves having a defined state of polarization, the lateral resolution can in itself only be obtained by an optical focussing system hich is contradictory to the concepts of both plane wave and a single angle of incidence. In the afore-mentioned article the lateral resolution of the order of 2 microns is obtained at the expense of a less satisfactory depth resolution.

The analysis of perturbations of the measurements due to the use of convergent rays has led the Applicant to calculate a compromise resulting in the conception of an ellipsometer of the rotating analyzer type having a satisfactory precision for the two afore-mentioned parameters. This compromise is a choice of a lateral resolution of the order of $10 \times 10$ microns with an angular aperture of the incident beam of the order of 4 to 5 degrees which permits of maintaining a sensitivity to the surface condition which is better than 1 Angström.

For such values of the angular aperture the wave can no longer be considered as being plane and the interpretation of results necessitates a new form of calculation.

In conventional ellipsometry the ratio of complex reflectance $\rho$ is measured as follows:

$$\rho = R_p R_s^{-1} = \tan\psi \exp(i\Delta) \qquad (1)$$

in which $R_p$ and $R_s$ denote the reflection coefficients of the linearly polarized waves having their polarization parallel and perpendicular, respectively, to the plane of incidence.

An ellipsometer of the rotating analyzer type permits directly measuring $\tan\psi$ and $\cos\Delta$:

$$\tan\psi = \left\|\frac{R_p}{R_s}\right\| \qquad (2)$$

$$\cos\Delta = \frac{R_e(R_p \cdot \bar{R}_s)}{\|(R_p \cdot R_s)\|} \qquad (3)$$

in which $R_e$ is the real part of a complex number.

In the case of a non-plane wave allowance must be made for the fact that the coefficients $R_p$ and $R_s$ are dependent on the angle of incidence $\theta$. The luminous incident beam is broken up into a sum of plane waves and the Fourier transform of its distribution is designated by g and that of the reflected and collected beam is designated by g'.

Thus the following formula is obtained for coherent light and for a homogeneous sample, in which formula the sign $*$ designates a convolution product:

$$\tan\psi = \frac{\|[R_p(\theta) * g \cdot g'(\theta)](\theta_o)\|}{\|[R_s(\theta) * g \cdot g'(\theta)](\theta_o)\|} \qquad (4)$$

in which $\theta_o$ = average angle of incidence and $$\cos\Delta = \frac{R_e[R_p(\theta) * g \cdot g'(\theta) \cdot (\bar{R}_s(\theta) * \bar{g} \cdot \bar{g}'(\theta)](\theta_o)}{\|R_p(\theta) * g \cdot g'(\theta)\| \cdot \|R_s(\theta)g \cdot g'(\theta)\|(\theta_o)} \qquad (5)$$

The formulas thus result from the previous formulas by replacing all the reflection coefficients by their convolution product with the function $g \cdot g'(\theta)$.

For incoherent light and for a homogeneous sample the formulas will be:

$$\tan\psi = \left( \frac{\|R_p(\theta)\|^2 * \|g \cdot g'(\theta)\|^2 (\theta_o)}{\|R_s(\theta)\|^2 * \|g \cdot g'(\theta)\|^2 (\theta_o)} \right)^{\frac{1}{2}} \qquad (6)$$

$$\cos\Delta = \frac{R_e(R_p(\theta) \cdot \bar{R}_s(\theta) * \|g \cdot g'(\theta)\|^2)(\theta_o)}{(A \cdot B)^{\frac{1}{2}}} \qquad (7)$$

with $A = \|R_p(\theta)\|^2 * \|g \cdot g'(\theta)\|^2 (\theta_o)$ $B = \|R_s(\theta)\|^2 * \|g \cdot g'(\theta)\|^2 (\theta_o)$ It is noted that in the case of a plane wave $g = g' = 1$ for $\theta = \theta_o$ and O for $\theta \neq \theta_o$ and the formulas (4) and (6) on the one hand and (5) and (7) on the other hand can be reduced to the formulas (2) and (3).

It is very important to be able to realise cartographic representations of a sample by means of such an ellipsometer by linear or two-dimensional scanning of the sample at a constant wavelength. The analysis of such cartographies can principally be carried out by studying the distribution of the points in the plane ($\tan\psi$, $\cos\Delta$), while the experimental points forming spatial trajectories can be confronted with theoretical trajectories corresponding to an assembly of calculated points for a given structural model obtained by varying one of the structure-related parameters. If this parameter is the thickness of a layer, a path which is referred to as thickness path is obtained.

The conventional ellipsometer is not used for the realisation of such cartographies and the sample supports of the known ellipsometers are not conceived for scanning the sample required to realise cartographic representations.

The invention has for its object to provide a spectroscopic ellipsometer comprising a sample support by means of which cartographic representations as mentioned hereinbefore can be realised.

To this end the spectroscopic ellipsometer according to the invention is characterized in that it comprises three translation plates, namely a first plate in accordance with a first direction, a second plate in accordance with a second direction perpendicularly to the first direction and being horizontal, intended for realising cartographic representations of the sample, as well as a third translation plate in accordance with a third direction perpendicular to the two other directions and intended for causing a point on the surface of the sample to coincide with the focal point, and in that it comprises at least two rotating plates, a first of which rotates about a first axis parallel to the first horizontal direction and a second of which rotates about a second axis parallel to the second direction with the two axes intersecting each other at a point coinciding with the focal illumination point so that the sample can be oriented by means of rotation in two orthogonal planes about the focal point.

The sample support can thus be positioned by acting on the third translation plate and on the first and second rotary plates so that the cartography is possible thanks to the first and second translation plates.

In a preferred embodiment the sample support is mounted on a rotary support having a vertical axis passing through the focal point, on which support the analysing device is mounted so that the angle of incidence can be modified.

In an advantageous embodiment the sample support comprises a third rotating plate supporting the sample and having a third axis of rotation perpendicular to the first and second axes so that the sample can be rotated in its own plane.

In an alternative embodiment the first rotating plate is mounted directly on the second rotating plate and the second and third translation plates are superposed in order on the second rotating plate, the third translation plate supporting the first translation plate which is integral with the sample.

Figure 2:
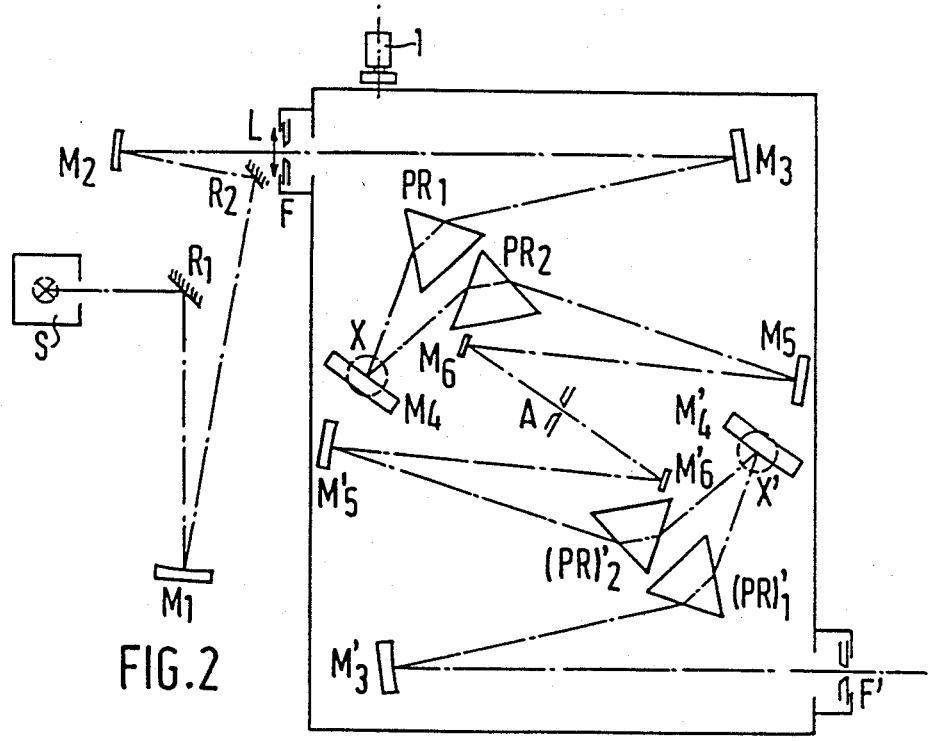
Figure 3:
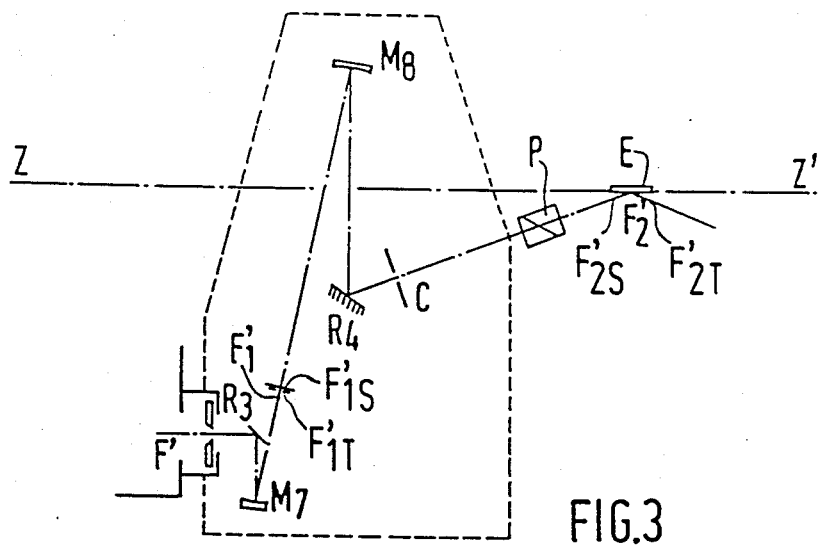
Figure 4:
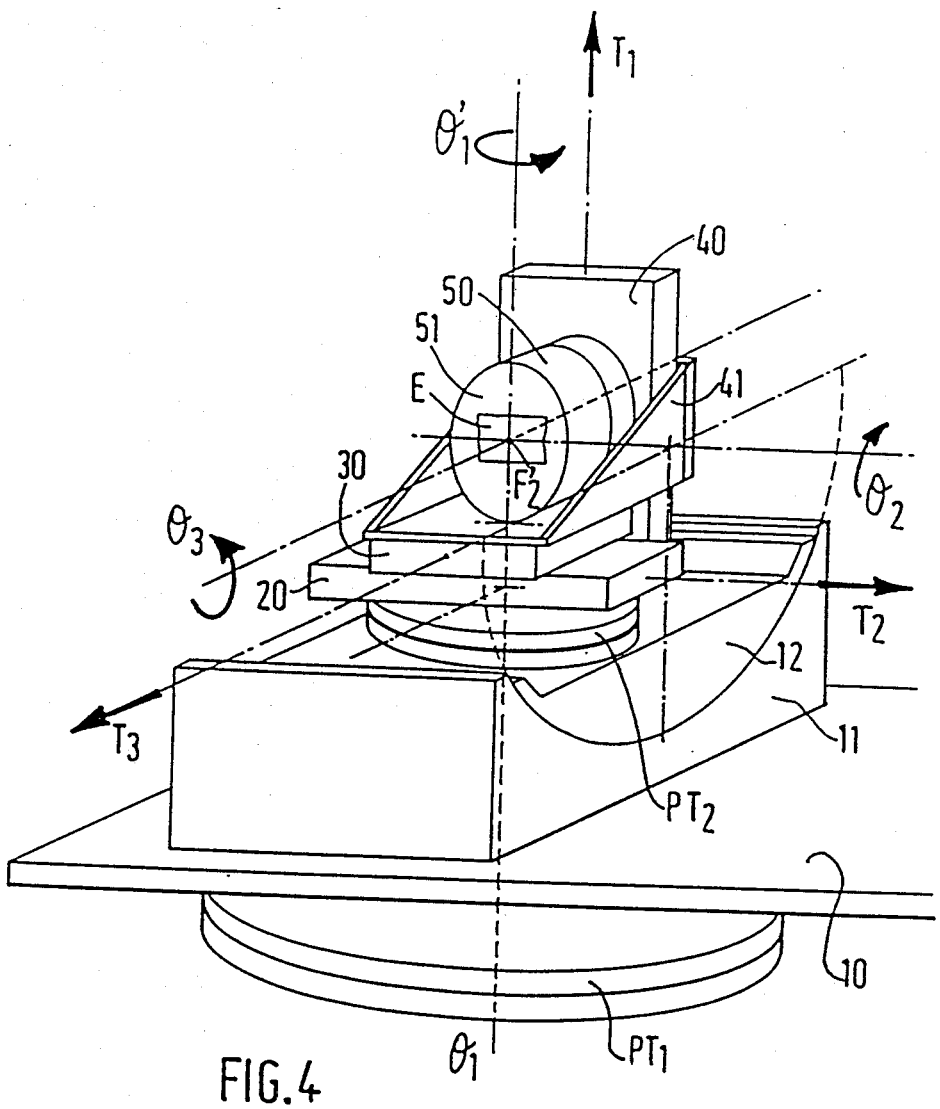

The invention will now be described in greater detail by way of example with reference to the accompanying drawings in which FIG. 1 shows the components of an incident field reflected on a plane surface, FIG. 2 shows a monochromator which can be used in an ellipsometer according to the invention, FIG. 3 shows an illumination arm according to the invention, FIG. 4 shows a sample support which can be used in an ellipsometer according to the invention and is suitable for cartographies, and FIG. 5 shoes an analysis arm comprising the sample support and a detection system.

Ellipsometry is an optical characterization method which is usually used in the reflection mode and at an oblique incidence. In contrast to a reflectivity measurement it does not measure the absolute value of an intensity but determines a state of polarization of the light. The response of the gas chosen is different depending on whether the electric field vector of the incident wave is parallel or orthogonal to the plane of incidence.

A plane wave having a polarization $E'_p$ which is parallel to the plane of incidence and forms an angle $\theta_o$ with the normal on the surface of the sample (FIG. 1) is reflected in the form of a wave having a polarization $E''_p$ which is submitted to a rotation of $\delta_p$ with respect to the incident wave. Similarly, a plane wave having a polarization $E'_s$ which is perpendicular to the plane of incidence is reflected in the form of a wave having a polarization $E''_s$ which is submitted to a rotation $\delta_s$ with respect to the incident wave.

The coefficients $R_p$ and $R_s$, see formula (1) are defined by the ratios:

$$R_p = \frac{E''_p}{E'_p} |R_p| e^{i\delta_p}$$

$$R_s = \frac{E''_s}{E'_s} = |R_s| e^{i\delta_s}$$

As the coefficients for a homogeneous sample are Fresnel coefficients, the result is that $\rho$ is a function of the angle of incidence as well as of the optical properties of the sample and thus of the wavelength. In the case of a non-homogeneous sample, which may have a laminated structure, $\rho$ is a function of the optical properties of each layer and their thicknesses. In the case of a spatially non-homogeneous sample $\rho$ is also a function of the lateral coordinates of the sample. These considerations show that the number of unknown parameters may rapidly become quite considerable.

Generally an ellipsometric measurement at a fixed wavelength does not permit an adequately precise analysis of the sample. It is thus interesting to use another parameter and in the special case it is the wavelength. Thus a spectroscopic ellipsometry is concerned.

FIG. 2 shows a monochromator with prisms having a high spectral resolution which are particularly suitable for the envisaged application. It includes a 900 W Xenon lamp as a luminous source S. Such a lamp has not only a good stability but also a continuous intensity in a large spectrum ranging from infrared (several microns) to ultraviolet (approximately 0.22 micron).

The entrance slit F of the monochromator is illuminated by an optical system of the KOHLER type. This system permits obtaining a uniform illumination. It comprises two spherical mirrors $M_1$ and $M_2$. The first mirror $M_1$ projects the image of the arc of the source S on the mirror $M_2$. The latter mirror conjugates the mirror $M_1$ on the entrance slit F of the monochromator. Two plane mirrors $R_1$ and $R_2$ maintain a small angle of incidence (approximately 5°) on the spherical mirrors $M_1$ and $M_2$. A lens L facing the entrance slit F is used for projecting the image of the arc formed on the mirror $M_2$ approximately to infinity in the monochromator.

The dispersive elements used are constituted by four double prisms of natural quartz $PR_1$, $PR_2$, $PR'_2$, $PR'_1$. This system is equivalent to two simple monochromators ($PR_1$,$PR_2$) and ($PR'_1$, $PR'_2$) arranged symmetrically with respect to a central slit A. Concave mirrors $M_3$ upstream of the prism $PR_1$ and $M_5$ downstream of the prism $PR_2$ for the simple monochromator and $M'_5$ upstream of the prism $PR'_2$ and $M'_3$ downstream of the prism $PR'_1$ for the second simple monochromator constitute two system at Z with equal angles of incidence. The system permits of conjugating the entrance slidt F, the central slit A and the exit slit F'. The wavelength is selected by means of two plane mirrors $M_4$ arranged downstream of the prism $PR_1$ and upstream of the prism $PR_2$ and $M'_4$ arranged downstream of the prism $PR'_2$ and upstream of the prism $PR'_1$. A stepper motor 1 causes the mirrors $M_4$ and $M'_4$ rotate simultaneously by means of a reduction gear unit. The stepper motor 1 is controlled by a computer in accordance with a precision calibration law permitting linear control of the wavelength.

FIG. 3 shows the optical illumination arm whose function according to the invention is to form a spot of small dimensions, for example of the order of 10 microns, on the surface of the sample. Since the ellipsometer is of the spectrosopic type, a device with spherical mirrors is used. As the spherical mirrors are used at an oblique incidence, they have a considerable astigmatism. The sagittal and tangential focal lengths are different. If an optical assembly is used which simply conjugates the exit slit F' of the monochromator and a point F'$_2$ of the surface of the sample, an image is obtained which is not focussed due to the astigmatism of the spherical mirrors. The astigmatism effects are corrected in accordance with FIG. 3. In this figure two spherical mirrors M$_7$ and M$_8$ are used, the mirror M$_7$ forming two images between F'$_{1T}$ and F'$_{1S}$ of the exit slit F' of the monochromator. The image F'$_{1S}$ is recaptured by the second adjustable mirror M$_8$ which conjugates the imagwe in two images F'$_{2S}$ and F'$_{2T}$ upstream and downstream of F'$_2$ and in the immediate vicinity of F'$_2$ with the surface of the sample. A second slit is situated in the plane of F'$_{1S}$ and is arranged perpendicularly thereto.

The astigmatism effects can be corrected by means of the controlled distance between the two afore-mentioned slits. Reflective plane mirrors R$_3$ and R$_4$ deflect the beam. The assembly is made more compact, inter alia, by choosing focal lengths for the mirrors M$_7$ and M$_8$ such that the optical system works with a magnification 2, which provides the possibility of arranging the fixed polarizer P at a suitable distance from the sample for which the part of the luminous beam corresponds to that of the polarizer P.

The fixed polarizer P is made of calcite and is integral with a calibration control unit constituted by a stepper motor by means of which the polarizer P can be oriented in advance to a measurement with a precision of electronic shutter C arranged between the reflective mirror R$_4$ and the polarizer P. In the closed position of the shutter C the continuous component can be subtracted from the ellipsometric signal, for example the component caused by the dark current of the detector.

According to FIG. 4 the support for the sample has two degrees of freedom of rotation about the axes $\theta_1$, $\theta_2$ and preferably a third degree of freedom about the axis $\theta_3$ and three degrees of freedom of translation in accordance with the axes T$_1$, T$_2$ and T$_3$.

The first degree of freedom of rotation is obtained by means of two coaxial rotary movements. The first rotary movement about the axis $\theta_1$ which passes through the focal point F'$_2$ is ensured by a small rotary plate PT$_1$ controlled by a micrometer screw not shown. The small plate PT$_1$ is integral with a plate 10 which supports both the support for the sample and the analyzing arm which will be described hereinafter (FIG. 5). The rotation of the small plate PT$_1$ makes it possible to choose the angle of incidence in a manner as described hereinafter.

A second small rotary plate PT$_2$ rotating about the axis $\theta'_1$ coinciding with the axis $\theta_1$ in the adjusting position makes it possible to orient the sample without changing the angle of incidence determined by the position of the first plate PT$_1$.

The second rotation about a horizontal axis $\theta_2$ is obtained with a precision of one hundredth degree by displacing a goniometric cradle 12 rotating in a support 11 mounted on the plate 10. The axis $\theta_2$ intersects the axis $\theta_1$ at the focal point F'$_2$. As a result the axis $\theta'_1$ always passes through the focal point F'$_2$.

The goniometric cradle 11 carries the second small plate PT$_2$ which in its turn carries the rest of the apparatus ensuring the three translations in accordance with the axis T$_1$, T$_2$, T$_3$ and the rotation about the axis $\theta_3$.

The translation according to the axis T$_2$ parallel to the axis $\theta_2$ is ensured by a plate 20 mounted on the rotary plate PT$_2$. The translation according to the axis T$_3$ perpendicular to the axis T$_2$ and to the axis $\theta'_1$ is ensured by a plate 30 mounted on the plate 20. Finally, the translation according to the axis T$_1$ parallel to the axis $\theta'_1$ is ensured by a plate 40 mounted on the plate 30 by means of a bracket 41 and carrying a rotary plate 50 with the axis $\theta_3$ parallel to the axis T$_3$. The sample is fixed on the front face 51 of the rotary plate 50 with which the sample can be rotated about its own axis. The sample can thereby be given a desired orientation in preferred directions (metallisation lines, etc.).

The translations T$_1$ and T$_2$ ensured by the stepper motors with an increment of 0.1 micron provide the possibility of realizing a cartographic representation of the sample once the surface of the sample is made to coincide with the focal point F'$_2$ by acting on the translation T$_3$. The translations T$_1$ and T$_2$ do not eliminate the setting. Since the axes $\theta'_1$, $\theta_2$ pass through the focal point F'$_2$, the point on the surface of the sample which coincides with F'$_2$ does not change irrespective of the adjustment of the three rotations $\theta'_1$ and $\theta_2$.

Figure 5:
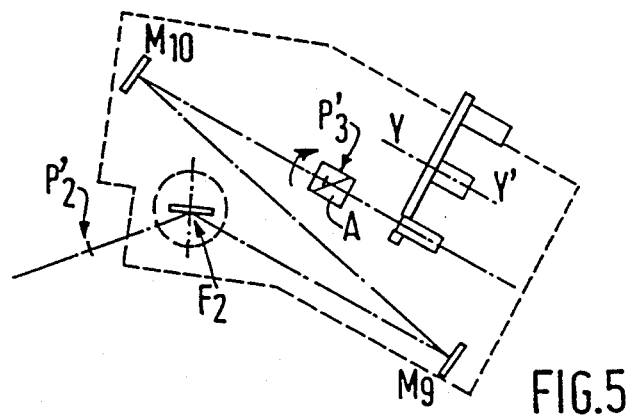

According to FIG. 5 the analysing arm which is integral with the movable plate can pivot in its plane around the axis $\theta_1$ (plate PT$_1$) which provides the possibility of modifying the angle of incidence and can also give the ellipsometer the "straight line" configuration in which there is no reflection on the sample. This makes it possible to align the assembly of the optical system as well as taking the reference for the measurement of the angle of incidence. The analyzing arm comprises the sample support as well as a detection system including an optical detection system which comprises two spherical mirrors M$_9$ and M$_{10}$ of identical focus, mounted at Z, a rotating analyzer and a turret provided with different detectors, an alignment laser and a sighting microscope.

The mirror M$_9$ picks up the luminous beam reflected by the sample and reflects it on the mirror M$_{10}$ for focussing on the detectors of the turret after passing through the rotating analyzer A. The angle of incidence on the mirrors M$_9$ and M$_{10}$ is also chosen to be as small as possible, more specifically about 6 degrees, so as not to disturb the polarization of the reflected light.

The rotating analyzer A is made of calcite and is mounted in the hollow branch of a direct current motor. An optical coder is integral with the axis of the motor.

The turret is rotatable about an axis YY' so that the different detectors supported by this turret can be placed in the optical path and it covers different spectral ranges similarly as the alignment laser and the sighting microscope. The detectors are recessed to some extent from the focal plane so that a uniform illumination of each detector is ecsured with the possible exception of detectors whose sensitive surface has small dimensions and which can be arranged in the focal plane.

The sighting microscope having a small magnification permits observing the sample through the optical analysis system as well as the adjustment of the position of the mirror M$_8$ and of the slit F'$_1$S. of the optical illumination arm.

The alignment laser, which is a He-Ne laser in this case, permits aligning the optical assembly comprising the sample support.

The signal I provided by the detector is sinusoidal at a frequency which is twice that of the rotating analyzer. If designates the angle of the rotating analyzer with respect to the axis p and P designates the angle of the polarizer with respect to the axis p, it holds that:

$$I = k(1 + \alpha_o \cos 2A + \beta_o \sin 2A)$$

with $$\alpha_o = \frac{\tan^2\psi - \tan^2 p}{\tan^2\psi + \tan^2 p}$$

$$\beta_o = \frac{2\tan\psi \tan P \cos\Delta}{\tan^2\psi + \tan^2 p}$$

in which $\alpha_o$ and $\beta_o$ are the normalized Fourier coefficients. The result is:

$$\tan\psi = \tan P \left(\frac{1 + \alpha_o}{1 - \alpha_o}\right)^{\frac{1}{2}}$$

$$\cos\Delta = \frac{\beta_o}{(1 - \alpha_o^2)^{\frac{1}{2}}}$$

The latter two equations show that the ellipsometric measurements may be summarized to some extent to measurements of the angles. In order that the measures have a good absolute precision it is important that all angles, namely the angle of incidence, the orientation of the polarizer and the marking of the position of the rotation analyzer are correctly determined. The orientation of the sample is also important because it determines the plane of incidence.

A calibration procedure of the ellipsometer, the analyzer arm, and thus the sample support shown in a straight-line configuration will now be described. The first operation is to adjust the position of the mirror $M_8$ and of the slit $F'_1S$ of the optical illumination arm with the aid of the sighting microscope. In the absence of the sample the beam of the laser arranged on the turret directly passes through the optical system in the inverse trajectory without being reflected. The position of the analyzing arm marked by the rotating plate $PT_1$ for which the laser beam passes through the center of all the mirrors is taken as a reference for measuring the angle of incidence. With the optical axis thus being realized for the laser beam, one acts on the rotations in accordance with the axes $\theta'_1$ and $\theta_2$ of the sample support in such a way that a perfect parallelism is obtained between the surface of the sample and the laser beam, that is to say the condition of grazing incidence. Subsequently one acts on the translation along the axis $T_3$ so that half the laser beam is shut off. This causes the focal point $F'_2$ of the illumination arm to coincide with a point on the surface of the sample. As an action on the rotations is accordance with the axes $\theta'_1$, $\theta_2$, $\theta_3$ (similarly as an action on the translations $T_1$ and $T_2$) does not change the position of the sample along the axis $T_3$, the adjustment can still be improved once the setting is realized.

After these adjustments the analyzing arm can be rotated and set to the measurment position. As the rotation of the small plate $PT_1$ is measured with a precision of one hundredth degree, the angle of incidence is thus precisely determined.

A perfect orientation of the surface of the sample can preferably be obtained by considering the signal detected by giving the assembly the measurement configuration. The rotating analyzer is brought to rotation at an angular frequency $\omega$. The detected signal has a frequency at a period of $2\omega$. An incorrect position of the sample with respect to the plane of incidence causes periodical terms of the frequency $\omega$ to appear in the signal. The alignment of the sample is thus realized by acting on the rotations $\theta'_1$ and $\theta_2$ so that the parasitic component of the frequency $\omega$ is eliminated. The visual examination of the signal on an oscilloscope by superposing two periods of the signal of the frequency $2\omega$ it possible to show all components of the frequency $\omega$.

The remaining degrees of freedom ($\theta_3$, $T_1$, $T_2$) no longer change the orientation of the plane of the sample. They provide the possibility of choosing the point to be measured on the sample (translations $T_1$ and $T_2$) and to realize cartographic representations thereof and in the case of a sample showing motives it is possible to align the latter (rotation $\theta_3$) parallel to a given direction, for example the horizontal or vertical direction.

The function of the degrees of freedom of the sample support can thus be summarized as follows:

the angle of incidence can be adjusted by means of the rotation $\theta_1$ the sample can be oriented with respect to the optical path by means of the rotations $\theta'_1$ and $\theta_2$ by rotating the sample in two orthogonal planes about the focal point $F'_2$.

the sample can be rotated by means of the rotation $\theta_3$ in its own plane about the axis passing through the focal point $F'_2$.

the translations $T_1$ and $T_2$ ensure the choice of the point on the sample which is to be measured.

the translation $T_3$ provides the possibility of bringing the sample in the plane of the focal point $F'_2$ while the thickness of the different samples can be taken into account.

Once the sample is positioned, the angular positions of the polarizer and the analyzer are to be marked. This can be done by minimizing the residual R defined by:

$$R = 1 - \eta^2(\alpha^2 + \beta^2)$$

in which $\eta^2$ is an attenuation coefficient produced by the electronic detection system filtering the signal supplied by the detector.

For measuring the residual the polarizer is manually positioned in the vicinity of the position p, namely at $p_o$. The value of the residual and the phase of the signal is measured at $2N+1$ equidistant points in the interval $p_o - \Delta p_o$, $p_o + \Delta p_o$. The variation of the residual around its minimum is approximated by a parabolic function whose coefficients are calculated by means of the smallest quadrant method.

This procedure makes it possible to position the polarizer with precision of the order of two hundredths of a degree and to determine all the necessary parametres for deriving the Fourier coefficients corrected for the attenuation and phase difference from the measured Fourier coefficients.

The attenuation $\eta^2$ is derived from the minimum value of $R = 1 - \eta^2$. This value depends on the time constant of the amplifier and the passband of the detector. For a photo-multtiplier, in which the passband is very large with regard to the modulation frequency, a time constant of 0.1 ms and a rotation frequency of 20 Hz for the rotating analyzer, the minimum value of R should be approximately 0.0004.

For measuring the phase difference the values of $\alpha$ and $\beta$ should be 1 and 0, respectively, when the polarizer is in the position p=O. The measurement of the Fourier coefficients α' and β' for p=O give the value of the phase difference φ:

$$\tan\phi = \frac{\alpha'}{\beta'}$$

To carry out the measurements the polarizer is offset through an angle given by the position p=O which is determined in the calibration phase.

What is claim is:

1. A spectroscopic ellipsometer comprising
   a sample,
   illumination means having a focal point for illuminating a surface of said sample at a given angle of incidence,
   analyzing means for analyzing light reflected from said surface of said sample, and
   sample support means for supporting said sample, said sample support means including structural means for adjusting said surface to provide a selected point on said surface in coincidence with said focal point,
   said sample support means further including
   three orthogonal translation plates for realizing cartographic representations of said sample, where a first translation plate extends in a first horizontal direction, where a second translation plate extends in a second horizontal direction, said second direction being perpendicular to said first direction, and where a third translation plate extends in a third direction perpendicular to said first and second directions, said third plate moving said selected point on said surface of said sample to coincide with said focal point, and
   at least two rotating plates, where a first of said rotating plates rotates about a first axis parallel to said first horizontal direction, and where a second of said rotating plates rotates about a second axis parallel to said second horizontal direction, said first axis and said second axis intersecting each other at a point coinciding with said focal point, said sample being oriented by rotation in two orthogonal planes about said focal point.

2. A spectroscopic ellipsometer according to claim 1, wherein said sample support means is mounted on a rotary support having a vertical axis passing through said focal point, said analyzing means being mounted on said rotary support to modify said angle of incidence.

3. A spectroscopic ellipsometer according to claim 1 or claim 2, wherein said sample support means also includes a third rotating plate, said third rotating plate having a third axis of rotation perpendicular to both said first axis and said second axis, said sample being rotatable in its own plane.

4. A spectroscopic ellipsometer according to claim 3, wherein said first rotating plate is mounted directly on said second rotating plate, and wherein said second and third translational plates are superposed in order on said second rotating plate, said third translational plate supporting said first translational plate integral with said sample.

5. A spectroscopic ellipsometer according to claim 4, wherein said third rotational plate is mounted on said first translational plate.

6. A spectroscopic ellipsometer according to claim 3, wherein said third rotational plate is mounted on said first translational plate.

7. A spectroscopic ellipsometer according to claim 1 or claim 2, wherein said first rotating plate is mounted directly on said rotating plate, and wherein said second and third translational plates are superposed in order on said second rotating plate, said third translational plate supporting said first translationsl plate integral with said sample.

* * * * *